(12) United States Patent
Goh et al.

(10) Patent No.: US 10,080,644 B2
(45) Date of Patent: Sep. 25, 2018

(54) TISSUE INTERFACE AUGMENTATION DEVICE FOR LIGAMENT/TENDON RECONSTRUCTION

(71) Applicants: National University of Singapore, Singapore (SG); Agency for Science, Technology and Research, Singapore (SG)

(72) Inventors: Cho Hong James Goh, Singapore (SG); Kok Hiong Thomas Teh, Singapore (SG); Pujiang Shi, Singapore (SG); Hoi Po James Hui, Singapore (SG); Jun Li, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 277 days.

(21) Appl. No.: 14/905,169

(22) PCT Filed: Jul. 21, 2014

(86) PCT No.: PCT/SG2014/000345
§ 371 (c)(1),
(2) Date: Jan. 14, 2016

(87) PCT Pub. No.: WO2015/009246
PCT Pub. Date: Jan. 22, 2015

(65) Prior Publication Data
US 2016/0157992 A1 Jun. 9, 2016

(30) Foreign Application Priority Data
Jul. 19, 2013 (SG) .............................. 201305559-5

(51) Int. Cl.
*A61F 2/08* (2006.01)
*A61L 27/36* (2006.01)
(Continued)

(52) U.S. Cl.
CPC ............ *A61F 2/08* (2013.01); *A61L 27/3604* (2013.01); *A61L 27/3834* (2013.01); *A61L 27/46* (2013.01);
(Continued)

(58) Field of Classification Search
CPC ................... A61F 2002/087; A61F 2002/0864
See application file for complete search history.

(56) References Cited

U.S. PATENT DOCUMENTS

| 5,245,012 A | 9/1993 | Lombari et al. |
| 7,727,575 B2 | 6/2010 | Kaplan et al. |

(Continued)

FOREIGN PATENT DOCUMENTS

| WO | WO200202461 A1 | 1/2002 |
| WO | WO2007020449 | 2/2007 |
| WO | WO2011041395 A2 | 4/2011 |

OTHER PUBLICATIONS

Liu et al., The interaction between a combined knitted silk scaffold and microporous silk sponge with human mesenchymal stem cells for ligament tissue engineering, Biomaterials 29 (2008) 662-674.*

(Continued)

*Primary Examiner* — Thomas J Sweet
*Assistant Examiner* — Megan Wolf
(74) *Attorney, Agent, or Firm* — K. David Crockett, Esq.; Niky Economy Syrengelas, Esq.; Crockett & Crockett, PC

(57) ABSTRACT

The present invention relates to a device for the interfacial augmentation of tissue grafts for the purpose of tendon and ligament reconstruction. The inventive device works both as a delivery vessel for osteoconductive and osteoinductive factors and as a scaffold to stimulate and support bone ingrowth and comprises a tubular composite silk sheath, said tubular composite silk sheath comprising: a backbone consisting of a tubular silk mesh, and a carrier material con- (Continued)

sisting of a porous silk sponge, wherein said tubular silk mesh consists of degummed silk fibroin fibers, wherein said porous silk sponge comprises silk fibroin fibers and hydroxyapatite particles and said tubular silk mesh and said porous silk sponge form a composite material. The present invention is also directed to a method for the manufacturing of such augmentation devices, a method for fixation of the thus fabricated tissue interface augmentation devices onto ligament or tendon grafts, a method for applying such devices for ligament and/or tendon reconstruction to tendon grafts, as well as their application in ligament and tendon reconstruction.

19 Claims, 3 Drawing Sheets

(51) Int. Cl.
    A61L 27/38    (2006.01)
    A61L 27/46    (2006.01)
    A61L 27/48    (2006.01)
    A61L 27/54    (2006.01)
    A61L 27/56    (2006.01)

(52) U.S. Cl.
    CPC ............... *A61L 27/48* (2013.01); *A61L 27/54* (2013.01); *A61L 27/56* (2013.01); *A61F 2002/087* (2013.01); *A61F 2210/0076* (2013.01); *A61F 2240/001* (2013.01); *A61L 2300/414* (2013.01)

(56) References Cited

U.S. PATENT DOCUMENTS

| | | | |
|---|---|---|---|
| 8,172,901 B2 | 5/2012 | Altman et al. | |
| 2010/0047309 A1* | 2/2010 | Lu | A61F 2/0811 424/423 |
| 2011/0046686 A1* | 2/2011 | Kaplan | A61F 2/2846 606/86 R |
| 2012/0187591 A1* | 7/2012 | Wang | A61K 9/5169 264/9 |
| 2012/0221104 A1 | 8/2012 | Altman et al. | |
| 2013/0073055 A1 | 3/2013 | Park et al. | |

OTHER PUBLICATIONS

Extended European Search Report dated Feb. 16, 2017 from European Application 14826226.4.
Spalazzi, et al., In Vivo Evaluation of a Tri-Phasic Composite Scaffold for Anterior Cruciate Ligament-to-Bone Integration, IEEE 525 (2006).
Song, et al., Failure of Osteointegration of Hamstring Tendon Autograft after Anterior Cruciate Ligament Reconstruction, 20 Arthroscopy: The Journal of Arthroscopic and Related Surgery 424 (Apr. 2004).
Schiavone, et al., Bone-Ligament Interaction in Patellar Tendon Reconstruction of the ACL, Knee Surg Sports Traumatol Anthroscopy 4 (1993).
Perez-Rigueiro, et al., Silkworm Silk as an Engineering Material, 70 Journal of Applied Polymer Science 2439 (1998).
Hogan, Bone Morphogenetic Proteins: Multifunctional Regulators of Vertebrate Development, 10 Genes & Development 1580 (1996).
Kratky, et al., An Unstable Lattice in Silk Fibroin, Nature 319 (1950).
Valuzzi, et al., Trigonal Crystal Structure of Bombyx Mori Silk Incorporating a Threefold Helical Chain Conformation Found at the Air-Water Interface, 29 Macromolecules 8606 (1996).
Lawrence, et al., Processing Methods to Control Silk Fibroin Film Biomaterial Features, 43 Journal of Material Sciences 6967 (2008).
Hu, et al., Regulation of Silk Material Structure by Temperature-Controlled Water Vapor Annealing, 12 Biomacromolecules 1686 (2011).

\* cited by examiner

TISSUE INTERFACE AUGMENTATION DEVICE FOR LIGAMENT/TENDON RECONSTRUCTION

FIELD OF THE TECHNOLOGY

The present invention relates to a device for the interfacial augmentation between tissue grafts and bone tissues for the purpose of tendon and ligament reconstruction. Moreover, the present invention is directed to a method for the manufacturing of such augmentation devices, a method for fixation of the thus fabricated tissue interface augmentation devices onto ligament or tendon grafts, a method for applying such devices for ligament and/or tendon reconstruction to tendon grafts, as well as their application in ligament and tendon reconstruction.

BACKGROUND ART

In the field of medicine, there has been an increasing need to develop implant materials for correction of biological defects. Particularly in the field of orthopedic medicine, there has been the need to replace or correct bone, ligament and tendon defects or injuries. As a result, there have emerged a number of synthetic implant materials, including, but not limited to, metallic implant materials and devices, devices composed in whole or in part from polymeric substances, as well as allograft, autograft, and xenograft implants. It is generally recognized that for implant materials to be acceptable, they must be pathogen free, and must be biologically acceptable. Generally, it is preferable if the implant materials are remodeled over time such that autogenous tissue replaces the implant materials. This goal is best achieved by utilizing autograft tissue from a first site for implantation into a second site.

Joint health is crucial for human mobility and the quality of life. Tendons and ligaments perform to translate and restrain motion respectively about a joint, making them important structures for proper joint functions. Taking the Anterior Cruciate Ligament (ACL) for example, it plays an important role in the normal functioning of the knee joint. However, ACL damage is prevalent as it affects 1 in 3000 Americans each year. When left untreated, the ligament degenerates with the onset of serious diseases such as osteoarthritis. Fortunately, ACL injuries can be addressed with tendon autografts. This treatment is hampered by the inferior integration between the tendon graft and the host bone. This integration site is known as the enthesis and its dysfunction has led to 3000-10000 revision surgeries annually in the United States alone.

To resolve this complication, a physiological understanding of the enthesis is essential. The native ACL anchorage site comprises of a gradient of fibrocartilaginous and calcified tissues that are constituted by a specific arrangement of cellular and Extra Cellular Matrix (ECM) components, which allow for the effective transmission of longitudinal and shear forces from the flexible ligament to the rigid bone. This complex anatomy is not recapitulated during conventional tendon transplantation and it constitutes the weakest region during the healing process. The native enthesis is usually replaced by a soft fibrous tissue, which does not provide adequate bony anchorage. Animal studies have demonstrated tendon pullout failure even after 12 weeks of ACL reconstruction. Spalazzi et al. stressed the need for optimal fibrovascular repair at the tendon bone insertion site to enhance the pull out strength of the graft (Spalazzi J P, Dagher E, Doty S B, Guo X E, Rodeo S A, Lu H H. In vivo evaluation of a tri-phasic composite scaffold for anterior cruciate ligament-to-bone integration. Conf Proc IEEE Eng Med Biol Soc 2006; 1:525-528.). In order to achieve this objective, various fixative methods with a prolonged resting time have been recommended. However, the resultant outcomes are still unsatisfactory.

Current techniques in promoting tendon osteointegration would include the use of specialized grafts and mechanical fixation. Yet, delayed healing and poor integration remained outstanding. Schiavone et al. experimented with a bone-patellar tendon-bone autograft in a rabbit model (Schiavone Panni A, Fabbriciani C, Delcogliano A, Franzese S. Bone-ligament interaction in patellar tendon reconstruction of the ACL. Knee Surg Sports Traumatol Arthrosc 1993; 1(1):4-8.). In their study, native osseous tissue was attached to both ends of the harvested patellar tendon as compared to none for conventional transplants. Interestingly, osseous integration was much longer than that anticipated for regular bone healing. It was reasoned that the healing process with the bone-patellar tendon-bone graft was more complicated than normal bone to bone fusion. To accelerate graft anchorage, mechanical fixation was employed. An example was the use of staples that secured the tendon graft outside the bone tunnel. However, a clinical study conducted by Song et al. (Song E K, Rowe S M, Chung J Y, Moon E S, Lee K B. Failure of osteointegration of hamstring tendon autograft after anterior cruciate ligament reconstruction. Arthroscopy 2004; 20(4):424-428.) indicated poor bonding even after 1.5 years of ACL reconstruction. This was attributed to the insufficient contact between the bone substratum and the tendon graft. Other mechanical means would include spiked washers, transfixation devices, sutures and tape fixation to buttons. Unfortunately, the outcomes were compromised by micromotion between the graft tissue and the surrounding bone. A gross indicator of transplant failure is bone tunnel expansion resulting from the osseous resorption at the insertion site, which occurs as early as 3 months after ACL reconstruction. Other complications would include ganglions, osseous edema, inflammations and sclerosis. These adverse effects were commonplace with commercially available mechanical implants that only provide temporary anchorage without enhancing biological fusion. Consequently, the functionality of the transplanted ACL is compromised thus resulting in the need for revision procedures.

Recently, a variety of materials and solutions have been proposed for improving the healing process of the bone-graft interface, including autologous bone tissue, cells, artificial proteins and calcium salts. One of the emerging materials are the calcium phosphates (CaP), which are known for their biocompatibility and are widely available commercially. Although CaPs have been shown to advance the healing of bone tunnel tissue in animal studies, it does not consist of a biological phase nor allows feasible incorporation of cells to the system. As such, the method is limited to being an osteoconductive approach, instead of an osteoinductive one. In other words, osteointegration will only depend on the native osteoblasts from the bone tunnel and not from within the interfacial CaP material.

Another method is the use of periosteum, harvested from the proximal tibia by a routine incision used to harvest hamstring tendons, to augment the graft-bone interface. This autologous material has the potential of improving tendon-bone healing, and may help to seal the intraarticular tunnel opening quickly after surgery and avoid reflux of synovial fluid into the tunnel. Bone tunnel enlargement could be reduced. Nevertheless, the periosteum will have to be autologous, limiting its application as an off-the-shelf product.

At present, the success of tendon or ligament transplantation techniques is severely curtailed by the poor anchorage of the grafts due to insufficient biological integration. Conventional fixative techniques emphasized mechanical bonding. However, there is need in the art for alternative strategies to improve ligament/tendon reconstruction.

SUMMARY OF THE INVENTION

The present invention overcomes some drawbacks of conventional therapies by promoting osteointegration at the bone-(tendon or ligament) graft interface within the surgically prepared bone tunnel such that accelerated healing can be achieved. To achieve this, the inventive device works both as a delivery vessel for osteoconductive and osteoinductive factors and as a scaffold to stimulate and support bone ingrowth. With the presence of osteogenic factors that are optionally incorporated into the tissue interface augmentation (TIA) device according to the present invention, mineralization of this interface tissue will be accelerated, leading to bone ingrowth into the tendon graft. Moreover, the presence of optionally seeded mesenchymal stem cells (MSCs) and/or other biologically active agents will also promote the reestablishment of continuous collagen fibers between the tendon and bone, thereby reestablishing the tendo-osseous junction. The delivery of cytokines and scaffold support provided by the TIA device is particularly essential for the tendon to firmly attach to the bone within the intra-articular environment. With the application of the inventive TIA device, it is anticipated that the bone-graft interface (reconstructed ACL's primary site of weakness) will not exist over extended durations long enough for complications to occur. Complications such as graft failure due to pull-out and micromotion leading to tunnel widening will be avoided with prompt bone-graft integration. Furthermore, firm attachment of the tendon graft to bone will allow earlier and more aggressive rehabilitation, leading to shorter recovery duration thus an earlier return to sports and work.

In a first aspect, the present invention provides for a tissue interface augmentation device for ligament and/or tendon reconstruction, comprising a tubular composite silk sheath, said tubular composite silk sheath comprising:
    a) a backbone consisting of a tubular silk mesh, and
    b) a carrier material consisting of a porous silk sponge, wherein said tubular silk mesh consists of degummed silk fibroin fibers, wherein said porous silk sponge comprises silk fibroin fibers and hydroxyapatite (HA; $Ca_{10}(PO_4)_6(OH)_2$) particles and said tubular silk mesh and said porous silk sponge form a composite material.

In another aspect, the present invention also relates to a method for manufacturing the tissue interface augmentation device for ligament and/or tendon reconstruction according to the invention, comprising:
    a) providing a tubular silk mesh;
    b) fitting an applicator tube into said tubular silk mesh to form an applicator-silk mesh assembly;
    c) inserting a stopper into the applicator tube of the applicator-silk mesh assembly;
    d) impregnating the tubular silk mesh with an aqueous silk solution comprising dispersed HA particles; and
    e) drying the applicator-silk mesh assembly impregnated with the aqueous silk solution comprising dispersed HA particles to form an applicator-composite silk sheath assembly.

In yet another aspect, the present invention is also directed to a method for applying the tissue interface augmentation device for ligament and/or tendon reconstruction according to the invention to a tendon graft, comprising:
    a) fitting one end of the tendon graft into or through the tubular space of an applicator tube;
    b) removing the applicator tube; and
    c) fixating the tubular composite silk sheath on the tendon graft.

DETAILED DESCRIPTION OF THE INVENTION

Figure 1:
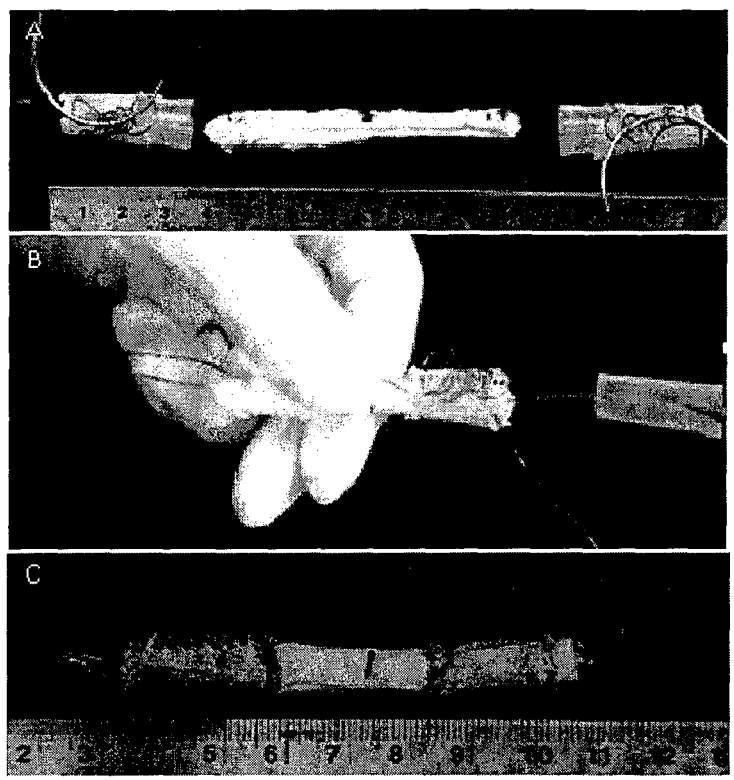
FIG. 1: Application process of silk sleeve onto tendon graft.
(A) Pre-application of TIA device; (B) Removal of tube applicator and securement of TIA device onto tendon graft; (C) Fully processed TIA-graft construct ready for surgical implantation.

As used in this specification, the singular forms "a," "an" and "the" include plural forms unless the context clearly dictates otherwise. Thus, for example, the term "a material" is intended to mean one or more materials, or a combination thereof.

"One or more", as used herein, relates to at least one and comprises 1, 2, 3, 4, 5, 6, 7, 8, 9 or more of the referenced species.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

In the event of a ruptured ligament/tendon, reconstruction using a tendon autograft is necessary and remains as the current gold standard. However, integration of the tendon graft with the surgically created bone tunnel remains a fundamental problem with this procedure, as success of currently applied transplantation techniques is severely curtailed by the poor anchorage of the tendon grafts due to insufficient biological integration. Conventional fixative techniques emphasize mechanical bonding without the use of biochemical precursors.

The present invention addresses and solves the problems of conventional therapies as in detail described herein. The purpose of the tissue interface augmentation (TIA) device according to the present invention is to complement the use of tendon grafts by promoting osteo-integration and -regeneration of the bone-graft interface within the bone tunnel such that an accelerated rate of healing can be achieved. The inventive device is designed to function as both a delivery vessel for osteoinductive and osteoconductive factors and a scaffold to promote and support bone ingrowth and enthesis regeneration.

One skilled in the art recognizes that by definition, a "tendon" is a collagenous cord that attaches muscle to its point of origin, typically to bone. By definition, a "ligament" is a band of collagenous tissue that connects bones or supports viscera.

The term "autograft" refers to graft material harvested from the same individual human who is also recipient of the graft, obtained surgically from non-essential "donation"-sites, such as, in case of bone to be harvested, the iliac crest. A "xenograft" is any kind of graft harvested from any species other than human, e.g. mammals, such as bovine or porcine tissue material. An "allograft" is a graft material harvested from an individual human, living or dead, which is not the recipient of the graft.

As used herein, the term "osteoconductive" refers to the ability (e.g., of a composition or material) to passively permit bone growth (e.g., onto and/or into the material). As such, osteoconduction can be characterized as a passive process. A material (e.g., a graft or implant) can be osteoconductive, for example, because it is configured to passively permit growth of bone on a surface of the material. In another example, a material can be osteoconductive because it is configured to passively permit growth of bone into an opening (e.g., a pore) of the material.

As used herein, the term "osteoinductive" refers to the capability (e.g., of a composition or material) to actively stimulate a biological response which induces bone formation. As such, osteoinduction can be characterized as an active process. Osteoinduction can include the formation and/or stimulation of osteoprogenitor cells, such as osteoprogenitor cells in bodily tissue surrounding or proximate to a graft or implant.

As used herein, the term "osteogenic" refers to the ability (e.g., of compounds such as growth factors) to induce osteogenesis. Osteogenesis is newly induced bone growth, which occurs due to viable osteoblasts. These either originate from (migrated and/or) differentiated osteoprogenitor cells or from the graft matrix material, into which they may have been embedded prior to implantation.

It is anticipated that the inventive device disclosed herein promotes bone ingrowth in the interfacial site of implantation between a porous carrier material comprising osteoconductive nano-particles and the surface of a bone tunnel, which has been drilled prior to graft insertion. Given the carrier materials' porous structure, invasive migration of vital osteoblasts into the carrier material is permitted and further promoted by nano-sized hydroxyapatite particles contained within the carrier material. It is thus furthermore anticipated that the inventive tissue interface augmentation device be replaced by newly generated bone tissue over time, and the tendon or ligament graft fixated inside the augmentation device thereby be firmly anchored to the bone by newly generated bone tissue resembling the native enthesis. This osteoconductive characteristic of the inventive device may be further supported and reinforced by the presence of osteogenic bone growth factors optionally embedded into the carrier material, which stimulate formation and differentiation of osteoprogenitor cells forming and thereafter mineralizing the organic bone matrix. In preferred embodiments of the present invention, optionally seeded mesenchymal stem cells (MSCs) sustain osteogenesis additionally. With hydrogel serving as a preservative carrier, autologous or allogeneic mesenchymal stem cells may be planted in the interfacial space between the inventive augmentation device and the tendon or ligament graft to complementarily generate bone matrix formation at this substantial and potential site of weakness in graft-to-bone attachment.

As described in detail herein, the inventive tissue interface augmentation device is thus purposefully designed to inherently implement and support the above-recited characteristics of osteogenesis. Different modular forms of the inventive device may be practically applied during surgical tendon or ligament replacement in a subject in need thereof, and will be described hereinafter extensively:

In a first embodiment of the present invention, the inventive tissue interface augmentation device for ligament and/or tendon reconstruction comprises a tubular composite silk sheath comprising a tubular silk mesh and a porous silk sponge. Together, both the tubular silk mesh and the porous silk sponge form a composite material, wherein the porous silk sponge serves as a carrier material for biologically active agents to be embedded therein.

The term "tubular", as referred to in this context, denotes any kind of tube-shaped form that features an inner, hollow space defined by an outer elongated, cylindrical shell, e.g. the silk mesh as defined above, with spherical, yet not obligatory circumferentially identical, distal openings. The tube may also be conical as long as there are openings at each end, for example such that the two distal openings have different diameters.

In the context of the present invention, the term "composite material" is to be understood to be denoting a material that has a backbone component, i.e. the silk mesh as defined above, to withstand mechanical stress exerted thereon and a carrier component, i.e. the silk sponge as defined above, to preserve and deliver biologically active agents and compounds contained therein. The term as used herein includes embodiments wherein two different materials contact each other, for example interpenetrate each other, without forming covalent linkages. Applied to the silk mesh and the silk sponge this may mean that the silk mesh lies within the silk sponge, with the sponge contacting and interpenetrating the silk mesh backbone.

As used herein, the term "biologically active" refers to the characteristic of naturally occurring, semi-synthetic, or synthetic therapeutic agent to provide one or more therapeutically desirable effect(s) when administered to a mammal (e.g., human).

According to the present invention, the silk mesh as part of the composite silk sheath serves as a backbone for the entire assembly to withstand mechanical stress during the bone tunnel pull-through, and is formed by, preferably, degummed silk, which can be formed as desired using a variety of techniques generally known in the art.

As generally known in the art, the term "silk" denotes the filamentous fiber product secreted by an organism. Silk has been shown to have the highest strength of any natural fiber, and rivals the mechanical properties of synthetic high performance fibers. Silks are also stable at high physiological temperatures and in a wide range of pH, and are insoluble in most aqueous and organic solvents. Silk is a protein, rather than a synthetic polymer, and its degradation products (e.g., peptides, amino acids) are biocompatible. Silk is non-mammalian derived and carries far less bio-burden than other comparable natural biomaterials (e.g., bovine or porcine derived collagen).

As used herein, the term "biocompatible" refers to the ability (e.g., of a composition or material) to perform with an appropriate host response in a specific application, or at least to perform without having a toxic or otherwise deleterious effect on a biological system of the host, locally or systemically.

Typically, in biomedical applications, only silk harvested from the silkworm is used. The fibroin produced by the silk glands of the silkworm is coated with sericin, a glue-like substance and immunogenic contaminant, which is removed by degumming the raw silk material. "Degumming", as used herein, thus refers to the removal of the sericin coat surrounding the fibroin filaments of the silkworm silk through washing or extraction in hot soapy water. Extracted and degummed fibroin is rather fragile and requires adequate workup in order to gain workable biomaterial for the design and development of medical devices (Perez-Rigueiro, J. Appl. Polymer Science, 70, 2439-2447 (1998); U.S. Pat. No. 5,252,285).

Alternatively, silk protein, for example in form of fibrils or fibers, suitable for use in the present invention may be obtained from a solution containing a genetically engineered silk, such as from bacteria, yeast, mammalian cells, transgenic animals or transgenic plants. See, for example, patent publications WO 97/03315 and U.S. Pat. No. 5,245,012.

Accordingly, the tubular silk mesh according to the present invention present may be prepared using a vast variety of different silk products, especially fibroin products. The tubular silk mesh may be a woven fabric, a non-woven fabric, a knitted product or a pressed product. In preferred embodiments of the present invention, the tubular silk mesh is a knitted silk mesh. In particular, although said silk mesh can be fashioned with any silk product, the most preferred silk product utilized is filamentous silk fibroin fiber, knitted into form as desired and degummed thereafter. However, the person skilled in the art understands that there exist different, combinatorial implementations of silk product and its shaping, all of which may be applicable in this context.

According to the present invention, the porous sponge as part of the tubular composite silk sheath consists of silk fibroin fibers, which, in preferred embodiments, may have been degummed beforehand to ensure optimal bio-compatibility, and further contains osteoconductive hydroxyapatite (HA; $Ca_{10}(PO_4)_6(OH)_2$) particles in the micro- and/or nano size range. Nanosize range, as used in this context, refers to particles have a diameter in their greatest dimension of about 1-100 nm. Microsize range, as used in this context, refers to particles sizes of more than 100 nm up to 50 μm. Preferably, the afore-mentioned particles are nearly spherical and/or have an aspect ratio of about 1-2.

Hydroxyapatite ($Ca_{10}(PO_4)_6(OH)_2$—"HA"), a calcium phosphate, is one of few bio-compatible mineral substances attracting a constant interest to its synthesis and properties. Different methods for synthesizing HA with different shape and size of crystals have been developed and are generally known in the art. Accordingly produced crystals of hydroxyapatite are utilized in medicine, especially in bone surgery, in the stomatology, as sorbent for medicinal preparation, in organic and inorganic chemistry and in gas-liquid chromatography.

Nano-hydroxyapatite (n-HA) according to the present invention refers, for example and without limitation, to nano-sized crystalline hydroxyapatite as, for example, disclosed in WO2002/002461 A1, with average dimensions of 0.06 μm±50% in length, 0.015 μm±50% in width and a thickness in the range between 0.000688 μm and 0.000814 μm depending on the direction of the symmetry axis of a crystallographic unit cell. Yet, the person skilled in the art recognizes that any kind of nano-sized hydroxyapatite crystal or particle is suitable for application in the context of the present invention, and no restrictions are meant to be applied by mention of suitable examples herein As already mentioned, the inventive device serves as both a delivery vessel and scaffold for osteoconductive, osteoinductive and osteogenic bone growth factors.

Osteoconductivity is mediated by the HA micro- and/or nanoparticles embedded in the silk sponge as well as the sponge's porous structure itself; allowing for enthesis regeneration and bone ingrowth into and thereby replacement of the inventive device over time.

Osteoinductivity and thereby osteogenesis may be promoted by one or more osteogenic growth factor(s), which is/are encapsulated in silk microspheres optionally embedded into the porous silk sponge, and which can be selected from the group consisting of BMPs (bone morphogenic proteins), VEGF (vascular endothelial growth factor), TGF-β (transforming growth factor-beta), and combinations thereof.

Osteogenic and chondrogenic proteins are able to induce the proliferation and differentiation of progenitor cells into functional bone, cartilage, tendon, and/or ligamentous tissue. These proteins, referred to herein as "osteogenic proteins," include members of the bone morphogenetic protein ("BMP") family identified by their ability to induce endochondral bone morphogenesis. The osteogenic proteins generally are classified in the art as a subgroup of the TGF-β superfamily of growth factors (Hogan, Genes & Development 10:1580-1594 (1996)). Osteogenic proteins include the mammalian osteogenic protein-1 (OP-1, also known as BMP-7) and its *Drosophila* homolog 60A, osteogenic protein-2 (OP-2, also known as BMP-8), osteogenic protein-3 (OP-3), BMP-2 (also known as BMP-2A or CBMP-2A) and its *Drosophila* homolog DPP, BMP-3, BMP-4 (also known as BMP-2B or CBMP-2B), BMP-5, BMP-6 and its murine homolog Vgr-1, BMP-9, BMP-10, BMP-11, BMP-12, GDF-3 (also known as Vgr2), GDF-8, GDF-9, GDF-10, GDF-11, GDF-12, BMP-13, BMP-14, BMP-15, GDF-5 (also known as CDMP-1 or MP52), GDF-6 (also known as CDMP-2), GDF-7 (also known as CDMP-3), the *Xenopus* homolog Vgl and NODAL, UNIVIN, SCREW, ADMP, and NEURAL.

Osteogenic proteins useful in this invention are selected from OP-2, OP-3, BMP-2, BMP-3, BMP-3b, BMP-4, BMP-5, BMP-6, BMP-9, BMP-10, BMP-11, BMP-15, GDF-1, GDF-2, GDF-3, GDF-6, GDF-7, GDF-8, GDF-9, GDF-10, GDF-11, DPP, Vg-1, Vgr-1, and 60A protein. As used herein, the terms "BMP," "osteogenic protein" and "osteogenic factor" embrace the class of proteins typified by human osteogenic protein 1 (hOP-1).

WO2011/041395 teaches the preparation of silk/PVA (polyvinyl alcohol) micro- and nanoparticles with controlled sizes and shapes, which are suitable for encapsulating numerous biologically active agents or chemicals therein, and are also suitable to be used as silk microspheres in the sense of the present invention. Given the silk particles' amphiphilic chemical nature, various kinds of drugs and compounds can be properly encapsulated into their porous interior space. These so entrapped active components, upon administration, are controllably and sustainably released to target organs or tissues in the patient's body. The spherical silk/PVA micro- or nanoparticles release their content upon hydration of hydrogen bonds between silk and polyvinyl alcohol molecules, which breaks up the protective capsule wall. Depending on the particle's size and form, but also on ratio and distribution of silk and PVA polymers, its native stability can be influenced and controlled. Biologically active agents and chemicals suitable for encapsulation and administration are, for example, cells (including stem cells), proteins, peptides, nucleic acids (e.g., DNA, RNA, siRNA), nucleic acid analogues, nucleotides, oligonucleotides or sequences, peptide nucleic acids (PNA), aptamers, antibodies or fragments or portions thereof (e.g., paratopes or complementarity-determining regions), antigens or epitopes, hormones, hormone antagonists, cell attachment mediators (such as RGD), growth factors or recombinant growth factors and fragments and variants thereof, cytokines, enzymes, antioxidants, antibiotics or antimicrobial compounds, anti-inflammation agents, antifungals, viruses, antivirals, toxins, prodrugs, drugs, dyes, amino acids, vitamins, chemotherapeutic agents, small molecules, and combinations thereof. The agent may also be a combination of any of the above-mentioned active agents.

In the context of the present invention, however, osteogenic growth factors such as BMPs, VEGF, TGF-β, which all have been specified above, as well as combinations thereof are preferred.

The silk microspheres encapsulating these growth factors are incorporated into the silk sponge and retained therein via chemical and/or chemo-physical (e.g. electrostatic) bonding of calcium and phosphate groups of the n-HA particles embedded in the silk sponge with amino acids of the silk protein molecules.

The inventive tissue interface augmentation device further comprises a tendon or ligament graft to be inserted and fitted into the tubular space of the tubular composite silk sheath.

A tendon or ligament graft is typically a collagenous material that is an autograft, allograft or xenograft. In the context of the present invention, preferably, the tendon or ligament graft is autotologous. Alternatively, the tendon or ligament graft may be made from another natural or synthetic material. In any case, in various embodiments, the tendon or ligament graft may be a predetermined length of tendon, a bundle of tendons of the same or different lengths, a predetermined length of ligament, a bundle of ligaments of the same length or different lengths, a segment or segments of pericardium, dermis, fascia, dura, skin, submucosal tissue (e.g., intestinal tissue), cartilage, or a combination thereof.

Typically, the source of the graft tissue is autograft, allograft, or xenograft. Most typically, the source of the tendon or ligament graft is autograft. However, in some situations, particularly in tendon repair, a tendon bundle comprising a xenograft tendon bundle or a combination of allograft and xenograft tendons of different thicknesses and lengths provides for enhanced performance under extreme stresses. Bundles refer to 1-10 discrete tendons or ligaments, which themselves can be made up of smaller fibers of tendons/ligaments that are crosslinked, stapled, glued, sutured, woven or braided.

"Fitting into" or "fitting through", in this context, refers to any kind of insertion technique resulting in a final localization of the tendon or ligament graft in the inside of the tubular composite silk sheath. This may include complete occupation of the inner tubular space within the composite silk sheath, whereby the tendon or ligament may but must not extend the distant opening end of the tubular sheath, thereby traversing the tubular silk sheath from one end of entry to its other distal end.

In order to be properly held in place during the implantation procedure, as well as for at least the time necessary for complete invasive bone tissue ingrowth into the inventive device, the tendon or ligament graft is in need of secure fixation to the composite silk sheath. Fixative methods applicable in this context include all kinds of mechanical attachment of organic graft tissue to a sturdy scaffolding, e.g. the tubular composite silk sheath according to the present invention, known in the art. Such methods may comprise, without limitation, stapling, suturing, gluing, clamping, tying, as well as the usage of nails, screws or bolts, and any combinations thereof. In preferred embodiments of the present invention, the tubular composite silk sheath is fixated on the tendon graft by suturing. For optimal fixation of the graft, suture thread is laced through the composite silk sheath from one end to the other. Suture thread suitable for this purpose may be any kind of suture thread generally known in the art for application during surgical suturing procedures. Suitable materials may be selected, without limitation, from the group consisting of naturally occurring materials such as silk, cotton or flax, as well as of synthetic materials, including absorbable polyglycolic acid, polylactic acid, monocryl and polydioxanone, but also non-absorbable nylon, polyester, PVDF (polyvinylidene fluoride), and polypropylene. Moreover, any combinations of the materials enlisted may be suitable for application in this context. Suture needle and excess suture is then cut and removed. The excess suture at the tail end may be retained to be utilized during the subsequent bone tunnel pull-through procedure (FIG. 1).

In case of a ligament graft to be implanted into a subject in need thereof, the respective ligament graft may be inserted into and fixated onto two individual tissue interface augmentation devices according to the present invention in a manner described herein. By doing so, a ligament graft with one individual TIA device on either far, opposite end of the ligament is obtained and readily implantable. That way, in the course of healing, the ligament is anticipated to be anchored and firmly attached to native bone tissue due to osteoconductivity, osteoinductivity and thereby osteogenesis initiated and supported by each individual TIA device on two distinct implantation sites simultaneously. The so inclined reader acknowledges, that each individual bon-graft interfacial augmentation device attached to a ligament graft may, but must not, bear distinctive features according to certain embodiments of the present invention. For instance, one TIA device fixated on a first end of the ligament may comprise only the tubular composite silk sheath formed by the tubular silk mesh and the porous silk sponge containing osteoconductive hydroxyapatite nano-particles. The second TIA device fixated on the other end of the respective ligament may further and additionally comprise silk microspheres encapsulating one or more osteogenic growth factor(s), which are embedded into the porous silk sponge of the respective second TIA device. However, this example given is to be understood as one of many possible combinatorial embodiments according to the present invention and is not intended to restrict or limit the scope of invention to this specific implementation.

In case of a tendon graft to be implanted into a subject in need thereof, the respective tendon graft is inserted into and fixated onto only one tissue interface augmentation device according to the present invention in a manner described herein. By definition, a tendon is a collagenous cord that attaches muscle to its point of origin, typically to bone. Consequently, only one end of the tendon graft is anticipated to be anchored and firmly attached to native bone tissue due to osteoconductivity, osteoinductivity and thereby osteogenesis initiated and supported by the inventive TIA device fixated thereon. The other end of the respective tendon is (re)attached to a muscle. In case of reattachment, methods for such an attachment are generally known in the art and exceed the scope of the present invention. However, in case of a tendon detached from its native bone junction, the tissue interface augmentation device according to the present invention may be fitted onto said tendon on its lose end and fixated thereon during surgery. The torn tendon may thus be reattached and, given the osteoconductive, -inductive and osteogenic properties of the inventive device, reconnected to the bone in resemblance to its original and native enthesis.

In another embodiment according to the present invention, the inventive tissue interface augmentation device may further comprise a hydrogel inserted into the interfacial space between tendon graft and tubular composite silk sheath. This hydrogel may comprise mesenchymal stem cells, which are anticipated to induce osteogenesis at the insertion site. Preferably, said hydrogel consists of a liquid alginate-based suspension, and further comprises calcium ions ($Ca^{2+}$) as the gelation agent. However, other types of divalent or trivalent metal ions are also suitable for this purpose. After fitting-through and proper positioning of the tendon or ligament graft, said hydrogel can be injected into the TIA-graft interfacial space. In preferred embodiments, $Ca^{2+}$ is employed after infusing the liquid alginate-based hydrogel system (ALG) containing mesenchymal stem cells into the space between the silk sheath and the tendon or ligament graft, to crosslink ALG (change from liquid to solid state/hydrogel) and secure the active components inside. Since gelation will occur within a very short duration, minimal leakage/seepage of the ALG suspension through the TIA device is anticipated.

Without wishing to be bound to any particular theory, it is believed that the seeded mesenchymal stem cells aid in propagating osteointegration from within the interfacial material. Yet, even in the acellular configuration (without mesenchymal stem cells), the tissue interface augmentation device may comprise cytokines that provide the biochemical cues necessary to promote osteoinduction.

The mesenchymal stem cells may be of allogenous source. Inherently, mesenchymal stem cells are non-immunogenic, and not only initiate activation of alloreactive T-cells without eliciting T-cell proliferative responses, but also actively suppress and inhibit T-cell responses to allogeneic cells by secretion of bioactive agents. The use of mesenchymal stem cells thus enables the inventive device to be made more readily off-the-shelf with maximum biocompatibility.

The hydrogel phase is conceived to be introduced at the point of application during surgery due to product storage considerations. As anticipated by the present invention, the mesenchymal stem cells contained within the alginate-based hydrogel system will further improve and accelerate osteointegration of the tendon autograft such that a firmer attachment is achieved.

Figure 5:
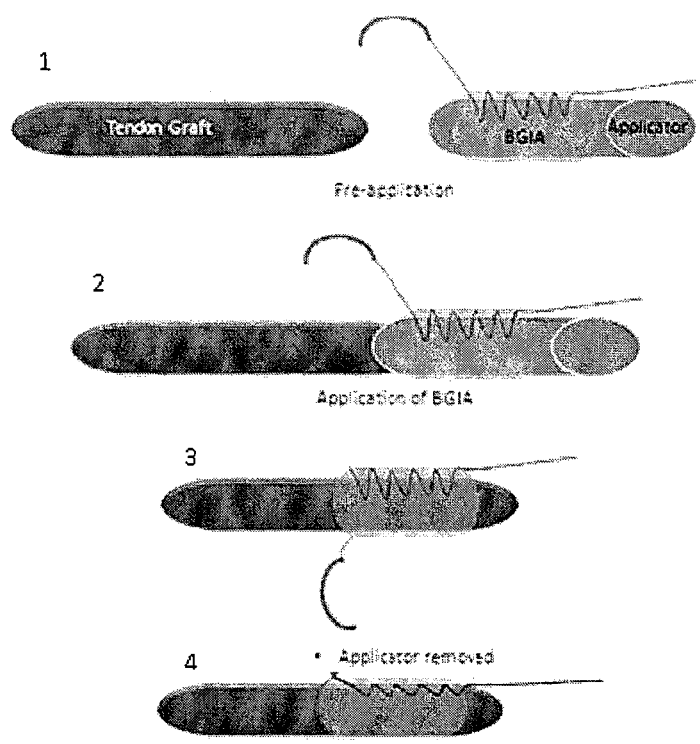
FIG. 5: Application steps of the TIA device onto tendon graft.
(1) Pre-application. TIA is packaged by wrapping over a tube applicator with suture being laced through for securement onto graft;
(2) Application of TIA. Tendon graft is fit into the tube applicator;
(3) Applicator removed: Tube applicator is removed and TIA device is positioned properly;
(4) Securement of lace by tightening suture at both ends. Suturing follows near the central section of tendon graft. Suture needle and excess suture is cut and removed.

The fitting-into or fitting-through of the tendon or ligament graft to be implanted into a subject in need of replacement may encompass, optionally, a removable, tubular formed applicator, which is able to snugly fit into the inner tubular space of the tubular composite silk sheath and facilitate the pull-through procedure of the graft (FIG. 5). To do so, preferably, said applicator tube may feature a smooth surface, and therefore may be selected from a group of materials, comprising, without limitation, synthetic materials such as plastics, metallic and metallic alloy materials, glass and ceramics. However, it is preferred that the applicator tube consist of a material sufficiently rigid to ensure support and give direction during the pull-through procedure, yet exhibits enough flexibility as not to hamper or prohibit gentle insertion of the tendon or ligament graft. The form of the applicator tube may be conical or non-conical. However, a conical shape of the applicator tube is preferred in the context of the present invention, as it facilitates both the insertion of a tendon or ligament graft through the wider opening end of the applicator tube and subsequent removal of the applicator alongside the length of the thus inserted graft tissue to obtain a graft-TIA device assembly.

Furthermore, the tissue interface augmentation device according to the present invention may comprise a stopper, which is shaped complementary to the applicator tube to function as a counterpart removably fitted into the tubular space of said applicator tube. Accordingly, said stopper may, but must not be, conically shaped. As will be described in more detail below, this stopper applies during the manufacturing process of the inventive TIA device. However, the stopper is intended to tightly yet easy-to-remove fit into the inner tubular space formed by the applicator tube and to, to a certain extent, completely occupy this inner space from one end to the other. This may, optionally, include the stopper extending either one or both opening ends of the tubular silk mesh. Preferably and especially in case of a conically shaped applicator tube, the stopper extends the wider opening end of the applicator, which enables easy handling and removal of the stopper. Materials that are suited to form such a stopper may, without limitation, be selected from the group consisting of synthetic materials such as plastics, metallic and metallic alloy materials, glass, ceramics, and rubber. However, the stopper material should be chosen in a manner to ensure easy removal of said stopper from the applicator tube without enhancing the likelihood of inflicting damage to the residual assembly.

The key step in the manufacturing process of the tissue interface augmentation device for ligament and/or tendon reconstruction according to the present invention is the formation of a porous silk sponge to be serving as a carrier material for nano-hydroxyapatite particles and, optionally, biologically active agents such as bone growth factors encapsulated in silk microspheres on and through the tubular silk mesh structure serving as a backbone. The manufacturing process of the inventive device firstly involves the fabrication of a tube-shaped silk mesh. Techniques for fabrication of such a mesh have already been listed above and may include, without limitation, for example weaving, knitting, pressing and the like. Preferably, the silk mesh is fabricated by knitting silk fibroin fibers into form as desired. After, optionally, degumming, the (degummed) knitted silk will then be loaded onto the applicator tube (FIG. 4D) and further incorporated with the stopper of a mould assembly (FIG. 4A-E). As described above, a stopper, may be any kind of plug fashioned in a manner to tightly yet removably fit into the inner tubular space of the applicator tube. Said stopper prevents significant amounts of silk fluid from entering the inside of the applicator tube, whereby silk sponge structure formation is anticipated to be proceeding only on and through the silk mesh sleeved onto the applicator tube beforehand. After that, the tissue interface augmentation device with applicator tube and removable stopper is further assembled with the mould base containing aqueous silk solution comprising silk protein and dispersed nano-hydroxyapatite (n-HA) particles, impregnated therewith, and then dried, preferably lyophilized, to form the silk composite sheath containing n-HA particles.

The term "impregnating" as referred to herein is to be understood as any kind of method known in the art, whereby a certain solid material is impregnated with a fluid in a way such that every surface of said solid material accessible is contacted, e.g. (permeated and) surrounded entirely, by said fluid. By definition, accessible surface in the context of the present invention also and especially includes surfaces of said solid material formed by porous and/or meshed structures. Impregnation of a solid meshed and/or porous structure thereby results in the solid material being, to a certain degree, permeated by the fluid. In this context, techniques for impregnating the material include, without limitation, dipping, including immersing, spraying, coating, and the like.

As a mould base, any kind of vessel suitable for holding and containing an aqueous solution and resistant to heat or cold, which may be applied during the drying process, may be utilized. Preferably, the mould base features a circular inner void in order to form a tubular sponge structure. Therefore, it is essential that the mould base is large enough to provide a gap between its inner vessel wall and the outer surface of the tubular silk mesh loaded onto the applicator-stopper assembly located inside said vessel (mould) to ensure complete engulfing of the silk mesh by the fluid silk solution.

The porous silk sponge is formed by drying of the aqueous silk solution comprising hydroxyapatite nano-particles. In this context, drying refers to any technique generally known in the art suitable for removal of the solvent, e.g. water, from the residual content of the initial solution. In preferred embodiments of the present invention, the aqueous silk solution is freed from its solvent by freeze drying (lyophilization), to form a porous silk sponge containing nano-hydroxyapatite particles. As the initial aqueous silk solution completely impregnated the tubular silk mesh sleeved onto the stopper-loaded applicator tube prior to drying, the newly formed porous silk sponge structure permeates the silk mesh, thus forming a tubular composite silk sheath, which, after removal of the applicator tube and/or stopper, features a hollow inner tubular space apt to accommodate a tendon or ligament graft.

The aqueous silk solution may contain 2.0-4.0% w/v of silk fibroin. Preferably, the aqueous silk solution contains 2% w/v of silk fibroin.

Silk fibroin is a polymorphous material existing in three different phases, commonly identified as silk I, II and III. Silk I represents a state of helical and random coil structures that is water-soluble and can be found in the glands of the silkworm prior to the spinning process or as (aqueous) silk solution (also known as regenerated silk). Silk II is characterized by its asymmetrical β-sheet structures in which hydrogen side chains from glycine are mainly exposed on one side of the β-sheet and hydrophobic methyl side chain from alanines on the other. (Kratky et al., Nature 165, 319-20 (1950)). As a consequence, β-sheets self-assemble by aligning side-by-side, stabilized by strong hydrogen bonds and van der Waals forces. Silk III, on the other hand, is a three-fold, helical conformation found in thin films at the air-water interface (Valluzzi et al., Macromolecules 29, 8606-14 (1996)).

By exposure to, for example, heat or shearing forces, a structural change from silk I to silk II is induced. This phase transition can also be obtained by the treatment of silk structures with methanol or other reagents that promote water loss from the silk molecules. As a consequence the transition from random coil (silk I) to β-sheet formation (silk II) is induced by enhanced chain-chain interactions. Beside the phase transition, this process also guarantees water-stable silk structures. Further processes to induce and control beta-sheet formation are steam-autoclaving (Park et al., J. Mat. Sci 43, 6967-6985 (2008)) and water annealing methods (Hu et al., Biomacromol. 12, 1686-1696 (2011)). The formation of a porous silk sponge structure is thus established by phase transfer from silk I to silk II by water removal.

After drying, preferably lyophilizing, the assembly comprising tubular silk sheath, applicator tube and stopper is removed from the mould and after extrication of the stopper from within the inner tubular space of the applicator tube, the thus obtained applicator-composite silk sheath assembly comprising the tubular silk mesh and the newly formed porous silk sponge can conveniently be handled with the applicator tube for subsequent tendon fixation as already described above.

Silk microspheres encapsulating osteogenic growth factors, as already described above, can subsequently be incorporated into the composite silk sheath after the drying step. The incorporation can be achieved by three mechanisms:
1. Direct blending of the silk microspheres into the silk solution and physical binding upon lyophilization,
2. Calcium and phosphate groups to anchor with special amino acids, or
3. Electrostatic attraction as the main mechanism of interaction between hydroxyapatite particles that are embedded in the silk sponge with the silk protein molecules of the silk microspheres.

Upon optimizing and selecting the mechanism for cytokine delivery suitable for use in the TIA device, it was observed that cytokine delivery via direct incorporation into the silk sponge phase was optimal. This was so as there was minimal encapsulated protein alteration and cytokine potency was retained. Moreover, the loading efficiency and distribution were better than through the use of the silk particles. The method of direct cytokine incorporation into silk sponge was thus utilized for fabrication of BMP-2 loaded TIA device in the in vitro assessment of various TIA device configurations.

To prepare subsequent graft fixation, in the case of suturing, surgical suture thread is laced through the tubular composite silk sheath from one end to the other. This may, but must not, be performed with the applicator tube still located inside the tubular inner space of the silk sheath. However, the applicator tube can be removed and, after suturing, be re-inserted into the silk sheath.

A method for application of a so manufactured tissue interface augmentation device according to the present invention comprises, as already described above, the secure attachment of said device to a tendon or ligament graft by, preferably, tightly suturing surgical suture thread laced through the composite silk sheath from one end to the other to the graft fitted into said silk sheath after removal of the applicator tube. For reasons of convenience, the suture thread may, but must not, be installed prior to graft insertion. According to certain embodiments, the MSCs-containing hydrogel may be inserted into the interfacial space between graft and TIA device. Such an approach has already been described herein above, and is preferably accomplished prior to graft fixation.

The tissue interface augmentation device according to the present invention is then fully processed and ready for administration to the patient (FIG. 1).

There exist constraints in the size of the tissue interface augmentation device, as the size of the bone tunnel remains a fundamental concern for minimally invasive surgical reconstruction of the ACL. Therefore, the tissue interface augmentation device should be as thin as possible to prevent excessive widening of the bone tunnel for the complete graft-bone-graft interfacial augmentation device construct to pass through. On the other side, with reduction of tissue interface augmentation device dimensions, the mechanical robustness of the tissue interface augmentation device will also be adversely affected. Hence, a balance will have to be made in terms of the tissue interface augmentation device's size and mechanical properties. In a preferred embodiment, the inventive tubular composite silk sheath has a diameter of 0.3 to 1.5 cm and/or a length of 1.5 to 5 cm.

Standard surgical procedures involving graft fixation and fitting (pulling) of the graft through the bone tunnel will follow. This includes provision of one or, in case of ligament implantation, two bone tunnel(s), in which one or two TIA devices with a graft fixated thereto are to be inserted. The bone tunnel(s) may, for example, be drilled. However, said bone tunnel(s) should be of suitable diameter and depth to ensure optimal, snug fit of the TIA device. Excess suture thread retained during fixation of the inventive device onto the graft may be utilized to facilitate insertion of the graft-TIA-assembly. Insertion may be accomplished by, for example, pulling said assembly through the bone tunnel provided beforehand. The excess suture thread may then be further utilized to fasten the graft to the bone by, for example, stapling, gluing, clamping, tying, as well as by usage of nails, screws or bolts, and any combinations thereof.

The tissue interface augmentation device according to the present invention is thus, as extensively described herein, intended and suited for reconstruction of a tendon or ligament in a subject in need thereof.

To date, prompt osteointegration of the tendon graft within the bone tunnel has been difficult with conventional therapies due to the lack of biochemical precursors.

In summary, the inventive tissue interface augmentation device provided by the present invention provides biochemical precursors including:
1. A temporary scaffolding material that helps to provide a snug fit to the bone interface. It prevents micromotion resulting in early inflammatory reactions, which lead to the onset of fibrosis. This matrix also serves as a delivery platform for cellular and bioactive components.
2. Progenitor cells, either seeded or attracted from the host into the porous tissue interface augmentation device, reconstitute the native cellular environment of the enthesis by differentiating into chondrocytes and osteoblasts. They not only deposit the necessary ECM but also cytokines that elicit regenerative response at the integration site.
3. The delivery of growth factors via the tissue interface augmentation device accelerate tissue restoration by triggering a migration of host reparative cells. These cytokines also induce cellular differentiation required for the formation of fibrocartilage and bony tissue at the anchorage site.

The novelty of the tissue interface augmentation thus lies in its ability to augment and improve graft to bone bonding via the incorporation of mesenchymal stem cells and osteogenic cytokines, while being resorbable at a rate compatible to that for bone regeneration. As such, graft integration to the bone tunnel will be accelerated to allow early and more aggressive rehabilitative procedures. Patients can thus benefit by being able to return to their normal activities more quickly. From the surgeon's perspective, the tissue interface augmentation device can be assembled with the tendon autograft easily and with minimal steps using the novel tube applicator.

The proposed solution will assist tendon grafting in patients whose ligaments/tendons are damaged by sporting injuries, trauma or wear and tear. It is estimated that 200,000 Americans sought ligament reconstruction annually and this number is expected to increase given the aging population and the popularity of sports. A reconstructive procedure cost US $25,000 approximately. This includes hospitalization and surgery but excludes indirect costs such as social benefits and work loss. The absence from work translates into a national social economic burden. This medical bill increases with corrective surgeries that address graft bond failures. Hence, conventional techniques are not cost effective given the necessity for future revision procedures. The inability to recover fully affects professional sportsmen. The abnormality results in the loss of an entire sporting season, inevitably career delays. Abstinence from physical exertion might be as long as 9 months. Moreover, it is recognized that athletes are never the same after the injury as they may not be able to compete at the highest levels of professional golf, soccer, basketball and other sports. It is likely that the TIA device can be applied in orthopedic reconstructive areas of the tendons/ligaments where recovery duration and integration quality of reconstructed ligaments/tendons matter.

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

EXAMPLES

Example 1

The TIA device was designed, developed and optimally fabricated using degummed knitted silk sleeve with low crystallinity nano-HA blended in the silk solution to form the sponge.

The knitted silk sleeve has three components: a knitted silk mesh, a silk sponge and low crystallinity nano hydroxyapatite (LHA). The knitted silk mesh was fabricated by using raw silk fibers with 24 needles on a knitting machine. Then, the knitted raw silk mesh was degummed to remove sericin thoroughly. The silk solution had a concentration of 6 wt.-% of silk fibroin in double distilled water. LHA was prepared by hydrothermal precipitation method: Briefly, calcium chloride, sodium phosphate tribasic and sodium carbonate were dissolved into the water individually at the same concentration. Calcium chloride and sodium phosphate were mixed together, then sodium carbonate was used to modify its crystallinity. The molar ratio of Ca:P:$CO_3$ was 1.67:0.8:0.2. Subsequently, the mixture was agitated at 25° C. overnight. LHA slurries are washed by water several times and collected by centrifugation. The slurries were mixed with 6% silk solution individually. The weight ratio of the inorganic materials and silk was 3-7. The particle size of LHA was around 80 nm. The knitted mesh was immersed in previously prepared LHA/silk (3/7, w/w) solution, subsequently frozen at 20° C. for 12 h and freeze-dried for 24 h to form the knitted silk sleeve. Thereafter, the knitted silk sleeve was immersed in methanol-water (90:10 v/v) solution for 10 min to induce β-sheet structural transition and then washed several times and air dried to remove the residual methanol.

A trial evaluation of the assembly process using the applicator unit in a typical clinical setting was performed (FIG. 1).

Figure 2:
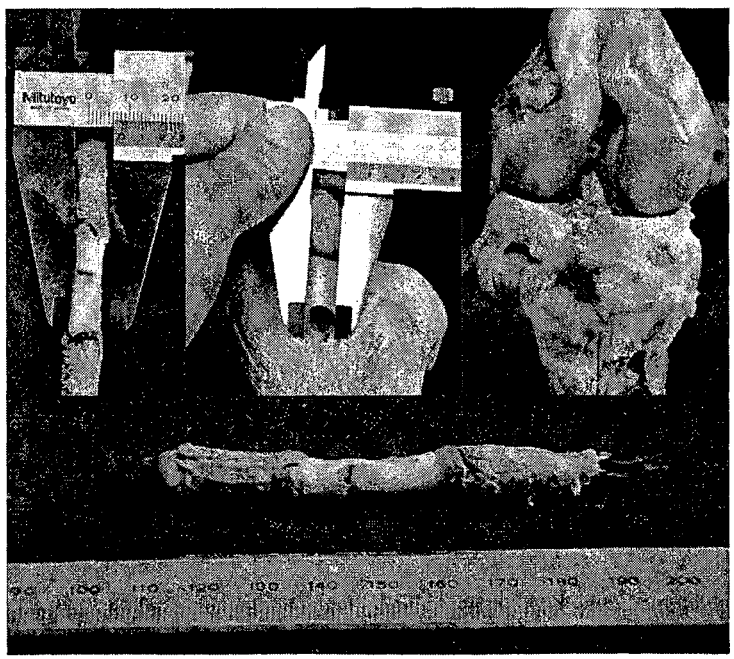
FIG. 2: TIA-secured porcine tendon graft of diameter 8.36 mm (A) and bone tunnel diameter of 8.00 mm (B). TIA-tendon complex secured for ACL reconstruction in the cadaveric pig knee (C). TIA appears intact after pull through procedure in the cadaveric pig knee (D).
Figure 3:
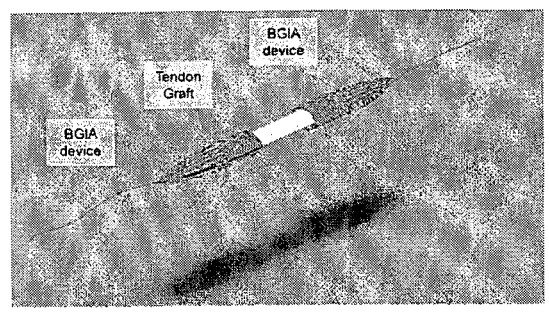
FIG. 3: Schematic diagram of TIA device applied onto both ends of tendon graft.
Figure 4:
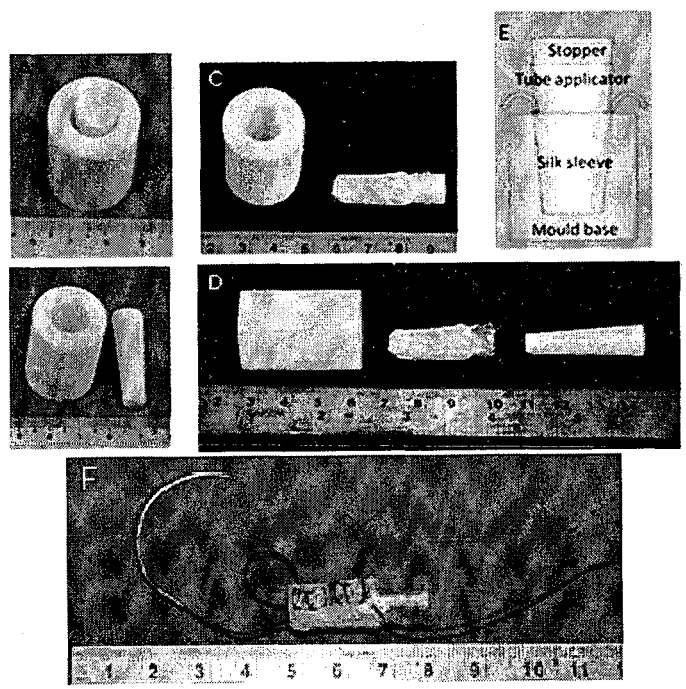
FIG. 4: Fabrication process of the TIA device using the mould assembly.
(A) Assembled mould; (B) Tube applicator assembled with stopper only prior to putting on silk sleeve; (C) Knitted silk sleeve applied onto tube applicator with stopper; (D) Stopper detached from tube applicator (with silk sleeve and silk sponge) after lyophilization process to form silk sponge; (E) Schematic view of mould assembly with silk sleeve. (F) Completed TIA device ready for sleeving onto tendon graft during ligament/tendon reconstruction surgery.

Upon application and securement of the TIA device onto a porcine tendon graft, a pull-through test was performed on the tendon-TIA complex using a typical tibial-femoral bone tunnel in the porcine cadaveric knee joint (FIG. 2), with convincing results indicating the robustness of the TIA device in withstanding typical ACL reconstruction procedure and the forces involved. The TIA-graft construct was also well secured and able to be loaded in typical knee flexion and extension process.

We claim:

1. Tissue interface augmentation device for ligament and/or tendon reconstruction, comprising a tubular composite silk sheath, said tubular composite silk sheath comprising:
   a) a backbone consisting of a tubular silk mesh, and
   b) a carrier material comprising a porous silk sponge, wherein said tubular silk mesh consists of degummed silk fibroin fibers, wherein said porous silk sponge comprises silk fibroin fibers and hydroxyapatite (HA; $Ca_{10}(PO_4)_6(OH)_2$) particles, and said tubular silk mesh and said porous silk sponge form a composite material; and
   an applicator tube removably fitted into a tubular space of the tubular composite silk sheath.

2. The device of claim 1, wherein the tubular silk mesh is a knitted silk mesh.

3. The device of claim 1, wherein the HA particles are osteoconductive HA micro- and/or nanoparticles.

4. The device of claim 1, wherein the carrier material further comprises silk microspheres.

5. The device of claim 4, wherein the silk microspheres contain osteogenic growth factors.

6. The device of claim 1, further comprising a tendon graft, wherein said tendon graft is configured to be fitted into the tubular space of the tubular composite silk sheath.

7. The device of claim 6, wherein the device comprises two tubular composite silk sheaths with each of the opposite ends of the tendon graft configured to be fitted into the tubular space of one of the two tubular composite silk sheaths.

8. The device of claim 6, wherein the device further comprises a hydrogel comprising mesenchymal stem cells (MSCs), with said hydrogel configured to be fitted in an interfacial space between tendon graft and tubular composite silk sheath(s).

9. The device of claim 1, wherein the applicator tube has a conical shape.

10. The device of claim 1, wherein the device further comprises a stopper removably fitted into a tubular space of the applicator tube.

11. The device of claim 1, further comprising a surgical suture thread laced through the composite silk sheath from one end to the other.

12. The device of claim 1, wherein the tubular composite silk sheath has a diameter of 0.3 to 1.5 cm and/or a length of 1.5 to 5 cm.

13. A method for manufacturing the tissue interface augmentation device for ligament and/or tendon reconstruction of claim 1, comprising:
   a) providing a tubular silk mesh;
   b) fitting an applicator tube into said tubular silk mesh to form an applicator-silk mesh assembly;
   c) inserting a stopper into the applicator tube of the applicator-silk mesh assembly;
   d) impregnating the tubular silk mesh with an aqueous silk solution comprising dispersed HA particles; and
   e) drying the applicator-silk mesh assembly impregnated with the aqueous silk solution comprising dispersed HA particles to form an applicator-composite silk sheath assembly.

14. The method of claim 13, wherein the impregnating step is carried out by fitting the applicator-silk mesh assembly into a mould containing the aqueous silk solution comprising dispersed HA particles.

15. The method of claim 13, wherein the drying step comprises lyophilizing the applicator-silk mesh assembly impregnated with the aqueous silk solution comprising dispersed HA particles.

16. The method of claim 13, further comprising the step of incorporating silk microspheres into the composite silk sheath after the drying step.

17. The method of claim 13, further comprising the step of lacing a surgical suture thread through the composite silk sheath from one end to the other.

18. Method for applying the tissue interface augmentation device for ligament and/or tendon reconstruction of claim 1 to a tendon graft, comprising:
   a) fitting one end of the tendon graft into or through a tubular space of the applicator tube;
   b) removing the applicator tube; and
   c) fixating the tubular composite silk sheath on the tendon graft.

19. The method of claim 18, wherein the fixating comprises suturing and/or tightening a suture lace, with said suture lace being comprised in the composite silk sheath before application.

\* \* \* \* \*